(12) United States Patent
Farooque et al.

(10) Patent No.: US 6,291,493 B1
(45) Date of Patent: Sep. 18, 2001

(54) TREATMENT OF SPINAL CORD INJURIES

(75) Inventors: Mohammad Farooque, Pembroke Pines, FL (US); David Jackson, Dunedin (NZ); Yngve Olsson, Uppsala (SE)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/367,665

(22) PCT Filed: Jun. 14, 1999

(86) PCT No.: PCT/SE99/01051

§ 371 Date: Aug. 17, 1999

§ 102(e) Date: Aug. 17, 1999

(87) PCT Pub. No.: WO99/65484

PCT Pub. Date: Dec. 23, 1999

(30) Foreign Application Priority Data

Jun. 15, 1998 (SE) .................................................... 9802119

(51) Int. Cl.⁷ ................................................. A61K 31/425
(52) U.S. Cl. ............................................................ 514/365
(58) Field of Search ............................................. 514/365

(56) References Cited

FOREIGN PATENT DOCUMENTS 9009174    8/1990    (WO) .

OTHER PUBLICATIONS

Biosis AN 999:81187, Farooque et al, Society for Neuroscience Abstracts, vol. 24,(1–2). abstract, 1998.*

Hedlund, B. et al. Chlormethiazole acts on chloride channels in cultured spinal cord neurons. *Neuroscience Letters* 78:217–221, 1987.

Smith, A. M. Emergencies in Palliative Care. *Annals of the Academy of Medicine* (Singapore), 23 (2): 186–190, 1994.

Gurusinghe, N. T. et al. Chlormethiazole in the management of post–craniotomy seizures. Acta *Psychiatr. Scand.* Suppl. 339, 73: 189–193, 1986.

Green, A. R. The Neuroprotective Actions of Chlormethiazole. *Progress in Neurobiology* 44: 463–484, 1994.

* cited by examiner

*Primary Examiner*—Rebecca Cook
(74) *Attorney, Agent, or Firm*—White & Case LLP

(57) ABSTRACT

The present invention relates to a new medical use of 5-(2-chloroethyl)-4-methylthiazole and the pharmaceutically acceptable salts and solvates thereof and pharmaceutical compositions containing it.

In particular, the present invention relates to the use of clomethiazole for the prevention and/or treatment of spinal cord injury.

8 Claims, No Drawings

TREATMENT OF SPINAL CORD INJURIES

FIELD OF THE INVENTION

The present invention relates to a new medical use of 5-(2-chloroethyl)-4-methylthiazole and the pharmaceutically acceptable salts and solvates thereof and pharmaceutical compositions containing it.

5-(2-chloroethyl)-4-methylthiazole is also known as clomethiazole, chlormethiazole, chlomethiazole, BAN Chlormethiazole and INN Clomethiazole. For the sake of simplicity the expression "clomethiazole" is used throughout the specification.

In particular, the present invention relates to the use of clomethiazole for the prevention and/or treatment of spinal cord injury.

BACKGROUND TO THE INVENTION

Preparations containing clomethiazole, particularly in the form of its acid addition salts, especially the acid addition salt with 1,2-ethanedisulfonic acid are known to possess valuable therapeutic properties. The general pharmacology and therapeutic applications of clomethiazole have been extensively reviewed in recent publications (see Acta Psychiatr Scand 73 (suppl 329), 1986; Progr. Neurobiol. 44, 463–484 (1994).Thus, for example, clomethiazole possesses sedative and hypnotic properties and is used clinically as a hypnotic in the elderly, particularly in the management of psychogeriatric patients. Clomethiazole also possesses anti-convulsant properties and is used clinically for the treatment of different types of convulsive states, such as, for example, status epilepticus and pre-eclampsias. Clomethiazole is also used clinically for the treatment of ethanol (alcohol) withdrawal states including delirium tremens. U.S. Pat. No. 5,399,572 discloses the use of clomethiazole in the prevention and/or treatment of neurodegeneration in pathological conditions such as stroke, cerebral ischaemia, hypoxia, epilepsy and neurodegenerative diseases such as Alzheimer's disease, multi-infarct dementia and Huntingdon's disease.

DESCRIPTION OF THE INVENTION

The present invention relates to the use of clomethiazole for the prevention and/or treatment of spinal cord injury.

In particular, the invention relates to the use of clomethiazole and the pharmaceutically acceptable salts and solvates thereof, in the prevention and/or treatment of pathological conditions caused by compression, either vertical or lateral, to the spinal cord, whether traumatically induced or due to compression due to other causes such as tumours, haemorrhage, infectious processes or spinal stenosis. Trauma may also induce spinal cord injury in the absence of any persistent compression of the cord. Impaired blood supply causing signs of spinal cord ischemia or infarction may also cause tissue destruction in the spinal cord.

Acute ischaemic stroke and its treatment differs substantially from trauma and other conditions which may entail compression of the spinal cord. The major existing treatment for traumatic spinal cord injury (methylprednisolone) is not an effective treatment for stroke. On the other hand, several compounds that are effective in stroke models are also effective in spinal cord compression injury models. Whether these compounds work in the clinic is unknown.

The present invention can be distinguished from the above prior art in that it is concerned with a new medical use which is unexpected and which can be clearly distinguished from the applications in the above described disorders. Given the current treatment for non-penetrating spinal cord injury (dexamethasone), usefulness of clomethiazole in any of the aforementioned indications could not lead to the suggestion that it should be useful in non-penetrating spinal cord injury.

DETAILED DESCRIPTION OF THE INVENTION

Different aspects of the present invention are:

The use of 5-(2-chloroethyl)-4-methylthiazole or a pharmaceutically acceptable salt or solvate thereof, in the manufacture of a medicament for the prevention and/or treatment of spinal cord injury;

a method for the prevention/and or treatment of spinal cord injury, comprising administration of a sufficient amount of 5-(2-chloroethyl)-4-methylthiazole or a pharmaceutically acceptable salt or solvate thereof; and a pharmaceutical formulation for use in the prevention and/or treatment of spinal cord injury, comprising 5-(2-chloroethyl)-4-methylthiazole or a pharmaceutically acceptable salt or solvate thereof as active ingredient.

Pharmaceutically acceptable salts include salts with 1,2-ethanedisulfonic acid, methanepolysulfonic acids, ethanesulfonic acid and ethanepolysulfonic acids.

The preferred pharmaceutically acceptable salt is diclomethiazole 1,2-ethanedisulfonate ((5-(2-chloroethyl)-4-methylthiazole)$_2$ 1,2-ethanedisulfonate) and is illustrated in the following structure.

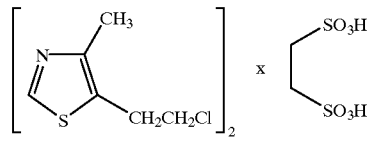

The effectiveness of 5-(2-chloroethyl)-4-methylthiazole or a pharmaceutically acceptable salt or solvate thereof for use according to the present invention in the prevention and/or treatment of spinal cord injury may be demonstrated by the ability to decrease the functional impairment following spinal cord injury induced by a period of compression of the spinal cord of rats. The detailed mechanisms that underlie the spinal cord damage and functional effects thereof have yet to be clarified in detail, but the above mentioned rat model test has been widely used as a predictive model of potentially active compounds.

It is a particular feature of the compound of the present invention that it can be administered simultaneously or soon after the spinal cord insult. It is expected that efficacy when administered soon after the insult is of particular relevance to the likely clinical utility.

Pharmaceutical Formulations

The administration in the novel method of treatment of this invention may conveniently be oral, rectal, or parenteral at a dosage level of, for example, about 1 to 3000 mg/kg, preferably about 10 to 1000 mg/kg and especially about 25 to 300 mg/kg and may be administered on a regime of 1 to 4 times a day. The dose will depend on the route of administration, a particularly preferred route being by intravenous infusion of an aqueous solution containing clomethiazole 1,2-ethanedisulfonate, for example, an aqueous solution containing clomethiazole 1,2-ethanedisulfonate 8 mg/ml. In this case, a steady state plasma concentration of between 0.1 and 500 $\mu$M will be achieved. It will be appreciated that the severity of the spinal insult, the age of the patient and other factors normally considered by the attending physician will influence the individual regime and dosage most appropriate for a particular patient.

The pharmaceutical formulations comprising the compound of this invention may conveniently be tablets, pills, capsules, powders or granules for oral administration; sterile parenteral solutions or suspensions for parenteral administration; or as suppositories for rectal administration Pharmacology Spinal Cord Damage Studies Spinal cord damage was induced in rats as described by Li et al (J Neurotrauma 12, 269 (1995) following generally accepted procedures.

Typical procedures and results are exemplified as follows:

Rats are anaesthetised, their temperature held steady and, after appropriate blood vessel cannulation, the laminae of Thoracic 7 and 8 vertebrae were removed leaving the dura intact. Maintaining respiration artificially and using appropriate surgery, compression was applied to the spinal cord for several minutes at a time and pressure that causes paraplegia of the hind limbs. After recovery from the surgery, hind limb motor functions are evaluated by observation and beam walking by a modification of generally accepted techniques described, for example, in Gale et al (1985; Exp Neurol 88, 123–134); von Euler et al (1996, Exp neurol 137, 242–254).

In the experiment described, clomethiazole was administered 30 minutes before compression as an intraperitoneal injection of 150 mg/kg.

Animals became paraplegic one day after injury. The rats were evaluated for hind limb motor function recovery over a period of 12 weeks and were then perfused/fixed for morphological investigations. MAP2 immunostaining was used to stain neurons and dendrites whereas luxol fast blue was used to stain myelinated tracts of the white matter. All animals recovered to some extent over the observation period of 12 weeks. However, hind limb motor function was better in the animals pre-treated with CMZ. The injured segment of the spinal cord showed severe atrophy, distortion, cavitation and necrosis of grey and white matter. The transverse sectional area was reduced to 32% in untreated animals and 38.5% in clomethiazole treated animals. MAP2 staining showed that grey matter was reduced to 20% in saline treated injured controls and to 47% in CMZ treated animals. This shows that clomethiazole has improved outcome after spinal cord damage.

What is claimed is:

1. A method for the prevention or treatment of spinal cord injury in a patient in need of said treatment, comprising the administration to the patient of a therapeutically effective amount of 5-(2-chloroethyl)-4-methylthiazole or a pharmaceutically acceptable salt or solvate thereof.

2. The method according to claim 1 wherein the spinal cord injury is caused by compression to the spinal cord.

3. The method according to claim 2 wherein the spinal cord injury is caused by traumatically induced compression to the spinal cord.

4. The method according to claim 1 wherein the spinal cord injury is caused by compression due to tumors, hemorrhage, infectious processes or spinal stenosis.

5. The method according to claim 1 wherein the spinal cord injury is caused by impaired blood supply.

6. The method according to any one of claims 1–5 wherein a pharmaceutically acceptable salt of 5-(2-chloroethyl)-4-methylthiazole is administered.

7. The method according to claim 6 wherein the pharmaceutically acceptable salt is diclomethiazole 1,2-ethanedisulfonate.

8. The method according to claim 1, wherein the patient is a mammal.

* * * * *